United States Patent
Kloos et al.

(10) Patent No.: US 8,883,199 B2
(45) Date of Patent: Nov. 11, 2014

(54) ADMINISTRATION REGIME FOR N-HYDROXY-4-{2-[3-(N,N-DIMETHYL-AMINOMETHYL)BENZOFURAN-2-YLCARBONYLAMINO]ETHOXY}BEN-ZAMIDE

(75) Inventors: Ioana Kloos, Rueil Malmaison (FR); Renata Robert, Suresnes (FR); Anne Jacquet-Bescond, Le Plessis Robinson (FR); Stephane Depil, Issy les Moulineaux (FR); Marylore Chenel, Paris (FR); Sylvain Fouliard, Paris (FR); Sriram Balasubramanian, San Carlos, CA (US)

(73) Assignees: Les Laboratoires Servier, Suresnes Cedex (FR); Pharmacyclics, Inc., Sunnyvale, CA (US)

( * ) Notice: Subject to any disclaimer, the term of this patent is extended or adjusted under 35 U.S.C. 154(b) by 0 days.

(21) Appl. No.: 13/605,116

(22) Filed: Sep. 6, 2012

(65) Prior Publication Data

US 2013/0064880 A1 Mar. 14, 2013

Related U.S. Application Data

(60) Provisional application No. 61/573,585, filed on Sep. 8, 2011.

(30) Foreign Application Priority Data

Sep. 8, 2011 (FR) ..................................... 11 02727

(51) Int. Cl.
| | | |
|---|---|---|
| *A61K 31/343* | (2006.01) | |
| *A61P 35/00* | (2006.01) | |
| *A61K 33/24* | (2006.01) | |
| *A61K 31/704* | (2006.01) | |
| *A61K 9/127* | (2006.01) | |
| *A61K 31/138* | (2006.01) | |

(52) U.S. Cl.
CPC .............. *A61K 31/343* (2013.01); *A61K 31/704* (2013.01); *A61K 33/24* (2013.01); *A61K 31/138* (2013.01)
USPC .............. 424/450; 514/469; 514/34; 424/649

(58) Field of Classification Search
None
See application file for complete search history.

(56) References Cited

U.S. PATENT DOCUMENTS

2009/0054720 A1* 2/2009 Sgouros et al. .................. 600/2

FOREIGN PATENT DOCUMENTS

WO WO-2004-092115 * 10/2004

OTHER PUBLICATIONS

"HDAC Inhibitor Phase I Trial in Advance Cancer—PCYC-0402", Pharmacyclics, 2010.
"PCI-24871—a novel and potent HDAC inhibitor Non-confidential overview", Oct. 1, 2009.
Buggy, et al., Mol. Cancer Ther., 2006, 5, 1309-1317.
Evens, et al., Blood (ASH Annual Meeting Abstracts), 2009, 114, Abstract 2726.
Fouliard, et al., European Journal of Cancer, 2013, 49, 2791-2797.
International Search Report for PCT/FR2012,052004 dated Nov. 29, 2012.
Lopez, et al., Clin. Cancer Res., 2009, 15, 3472-3483.
Thomas, et al., Cancer Research, 2011, vol. 71, Issue 8, Supplement 1. Abstract 2631.
US National Institutes of Health: "PCYC-0401: Study of the Tolerability, Safety, and Pharmacokinetics of CRA-024781 in Cancer Patients", Clinical Trials.gov, Aug. 24, 2010.
US National Institutes of Health: "PCYC-0402: Study of the Safety and Tolerability of Oral Capsule Form of PCI-24781 in Advanced Cancer Patients", Clinical Trials.gov, Sep. 26, 2012.

* cited by examiner

*Primary Examiner* — Frederick Krass
*Assistant Examiner* — Celeste A Roney
(74) *Attorney, Agent, or Firm* — Hueschen and Sage

(57) ABSTRACT

N-hydroxy-4-{2-[3-(N,N-dimethylaminomethyl)benzofuran-2-ylcarbonylamino]ethoxy}-benzamide of formula (I):

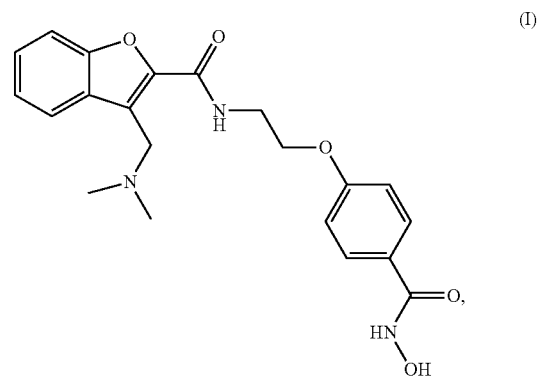

or an addition salt thereof with a pharmaceutically acceptable acid or base, alone or in association with surgery, chemotherapy or hormone therapy treatment or radiotherapy, for use in the treatment of cancer, characterized in that it is administered for 4 consecutive days, that period being followed by 3 consecutive days without any administration of compound of formula (I), with the proviso that the chemotherapy is not FOLFOX.

10 Claims, 2 Drawing Sheets

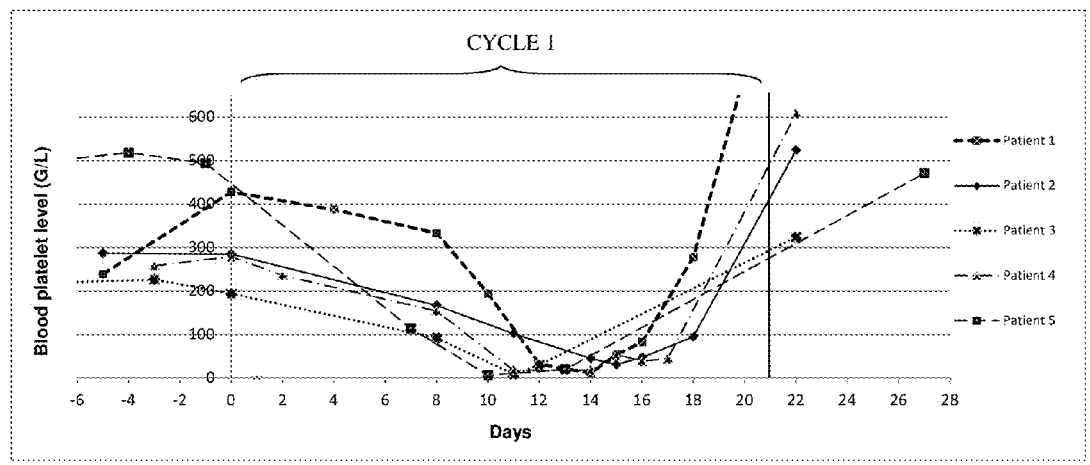
Figure 1: Changes in platelet levels for administration regime 1
*(75 mg/m² of N-hydroxy-4-{2-[3-(N,N-dimethylaminomethyl)benzofuran-2-yl-carbonylamino]ethoxy}benzamide hydrochloride administered twice daily for 14 consecutive days followed by 7 days without treatment)*

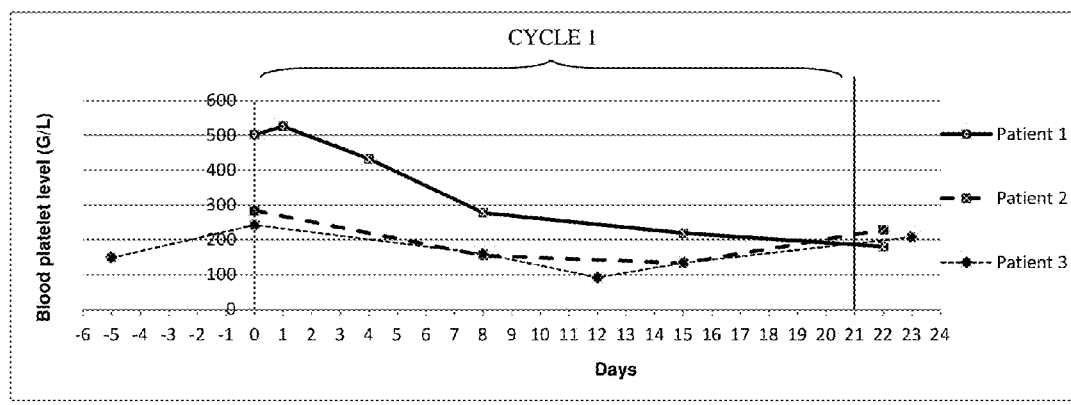
Figure 2: Changes in platelet levels for administration regime 2
*(75 mg/m$^2$ of N-hydroxy-4-{2-[3-(N,N-dimethylaminomethyl)benzofuran-2-yl-carbonylamino]ethoxy}benzamide hydrochloride administered twice daily for 4 consecutive days followed by 3 days without treatment)*

ADMINISTRATION REGIME FOR N-HYDROXY-4-{2-[3-(N,N-DIMETHYLAMINO-METHYL)BENZOFURAN-2-YLCARBONYLAMINO]ETHOXY}BENZAMIDE for N-hydroxy-4-{2-[3-(N,N-dimethylaminomethyl)benzofuran-2-ylcarbonylamino]ethoxy}benzamide of formula (I):

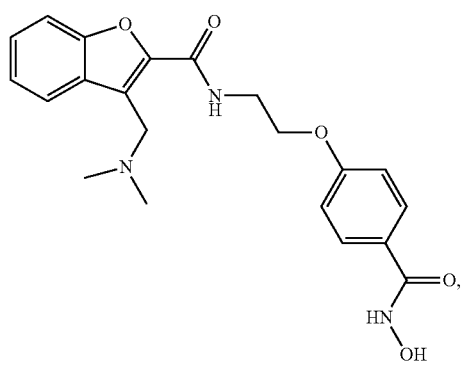

or an addition salt thereof with a pharmaceutically acceptable acid or base, alone or in association with surgery, chemotherapy or hormone therapy treatment or radiotherapy, for the treatment of cancer.

N-hydroxy-4-{2-[3-(N,N-dimethylaminomethyl)benzofuran-2-ylcarbonylamino]ethoxy}-benzamide is a powerful histone deacetylase (HDAC) inhibitor described in patent application WO2004/092115. It allows inhibition of cell growth and induces apoptosis in cultured tumour cells in vitro, and it inhibits tumour growth in vivo in xenograft models (Buggy et al., *Mol. Cancer Ther* 2006 5(5) 1309). Its pharmacological profile makes it of major therapeutic value in the treatment of cancer.

In the present invention it has been established that N-hydroxy-4-{2-[3-(N,N-dimethylaminomethyl)benzofuran-2-ylcarbonylamino]ethoxy}benzamide of formula (I) has a very advantageous therapeutic index in the treatment of cancer when it is administered for 4 consecutive days, that period being followed by 3 consecutive days without any administration of compound of formula (I).

More specifically, it has been shown that the maximum tolerated dose of N-hydroxy-4-{2-[3-(N,N-dimethylaminomethyl)benzofuran-2-ylcarbonylamino]ethoxy}benzamide was considerably increased in patients suffering from cancer when it was administered for 4 consecutive days, that period being followed by 3 consecutive days without any administration of compound of formula (I). That administration cycle is repeated as many times as necessary for the cancer treatment. Alternatively, those weekly administration cycles may be periodically broken up by a week without any treatment.

This administration regime makes it possible to envisage better use of the N-hydroxy-4-{2-[3-(N,N-dimethylaminomethyl)benzofuran-2-ylcarbonylamino]ethoxy}benzamide in that it makes it possible to minimise the platelet toxicity inherent to the product whilst allowing sufficient exposure for the cancer treatment.

The present invention relates to N-hydroxy-4-{2-[3-(N,N-dimethylaminomethyl) benzofuran-2-ylcarbonylamino]ethoxy}benzamide of formula (I):

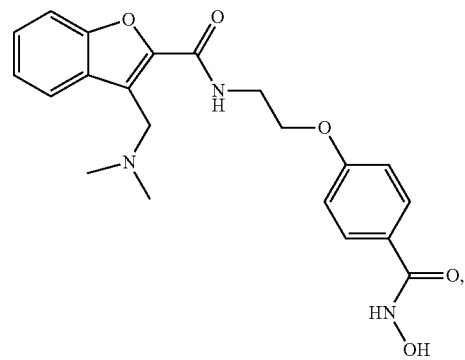

or an addition salt thereof with a pharmaceutically acceptable acid or base, alone or in association with a surgery, chemotherapy or hormone therapy treatment or radiotherapy, for use in the treatment of cancer, characterised in that it is administered for 4 consecutive days, that period being followed by 3 consecutive days without any administration of compound of formula (I), with the proviso that chemotherapy is not FOLFOX.

The present invention relates to N-hydroxy-4-{2-[3-(N,N-dimethylaminomethyl) benzofuran-2-ylcarbonylamino]ethoxy}benzamide of formula (I):

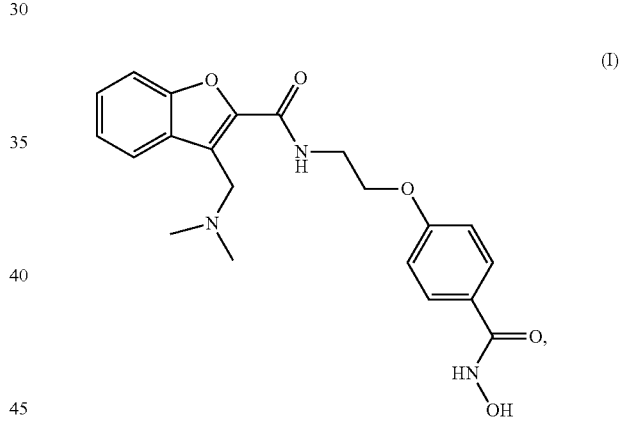

or an addition salt thereof with a pharmaceutically acceptable acid or base, alone or in association with surgery, chemotherapy or hormone therapy treatment or radiotherapy, for use in the treatment of cancer, characterised in that it is administered for n+1 consecutive days, that period being followed by n consecutive days without any administration of compound of formula (I), with the proviso that chemotherapy is not FOLFOX, wherein n is any integer between 1 and 10, for example, 1, 2, 3, 4, 5, 6, 7, 8, 9, or 10. In some embodiments, n is 3.

The present invention relates to N-hydroxy-4-{2-[3-(N,N-dimethylaminomethyl) benzofuran-2-ylcarbonylamino]ethoxy}benzamide of formula (I) or an addition salt thereof with a pharmaceutically acceptable acid or base, alone or in association with surgery for use in the treatment of cancer, characterized in that the compound of formula (I) is administered for 4 consecutive days, that period being followed by 3 consecutive days without any administration of the compound of formula (I).

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of cancer, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is cisplatin-doxorubicin-cyclophosphamide. In certain embodiments, the chemotherapy is pegylated liposomal doxorubicin and cisplatin.

The present invention relates to N-hydroxy-4-{2-[3-(N,N-dimethylaminomethyl) benzofuran-2-ylcarbonylamino]ethoxy}benzamide of formula (I) or an addition salt thereof with a pharmaceutically acceptable acid or base, alone or in association with a hormone therapy treatment for use in the treatment of cancer, characterized in that the compound of formula (I) is administered for 4 consecutive days, that period being followed by 3 consecutive days without any administration of compound of formula (I). In some embodiments, the hormone therapy treatment is tamoxifen.

The present invention relates to N-hydroxy-4-{2-[3-(N,N-dimethylaminomethyl) benzofuran-2-ylcarbonylamino]ethoxy}benzamide of formula (I) alone or in association with radiotherapy for use in the treatment of cancer, characterized in that the compound of formula (I) is administered for 4 consecutive days, that period being followed by 3 consecutive days without any administration of compound of formula (I).

In the context of the invention, preference is given to using the N-hydroxy-4-{2-[3-(N,N-dimethylaminomethyl)benzofuran-2-ylcarbonylamino]ethoxy}benzamide in the form of a hydrochloride.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of cancer, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of cancer, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin.

In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of cancer, characterized in that the compound of formula (I) is administered for 4 consecutive days, that period being followed by 3 consecutive days without any administration of compound of formula (I). In some embodiments, the hormone therapy treatment is tamoxifen.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with radiotherapy for use in the treatment of cancer, characterized in that the compound of formula (I) is administered for 4 consecutive days, that period being followed by 3 consecutive days without any administration of compound of formula (I).

The N-hydroxy-4-{2-[3-(N,N-dimethylaminomethyl)benzofuran-2-ylcarbonylamino]-ethoxy}benzamide is advantageously administered for 4 consecutive days at the rate of 2 administrations per day, that period being followed by 3 consecutive days without any administration of compound of formula (I).

In certain embodiments, the cancer treated according to the administration regime of the invention may be a carcinoma, a tumour, a neoplasm, a lymphoma, a melanoma, a glioma, a sarcoma or a blastoma. Examples of carcinomas include, but are not limited to, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis. The administration regime according to the invention is especially useful in the treatment of solid tumours, and even more especially in the treatment of breast cancer. Epithelial ovarian, fallopian tube and primary peritoneal carcinoma are also specifically targeted.

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of breast cancer, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of breast cancer, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to N-hydroxy-4-{2-[3-(N,N-dimethylaminomethyl)benzofuran-2-ylcarbonylamino] lethoxy}benzamide of formula (I) or an addition salt thereof with a pharmaceutically acceptable acid or base, alone or in association with a hormone therapy treatment for use in the treatment of breast cancer, characterized in that the compound of formula (I) is administered for 4 consecutive days, that period being followed by 3 consecutive days without any administration of compound of formula (I). In some embodiments, the hormone therapy treatment is tamoxifen.

The present invention relates to N-hydroxy-4-{2-[3-(N,N-dimethylaminomethyl)benzofuran-2-ylcarbonylamino] ethoxy}benzamide of formula (I) alone or in association with radiotherapy for use in the treatment of breast cancer, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of breast cancer, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of breast cancer, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of breast cancer, characterized in that the compound of formula (I) is administered for 4 consecutive days, that period being followed by 3 consecutive days without any administration of compound of formula (I). In some embodiments, the hormone therapy treatment is tamoxifen.

The present invention relates to the HCl salt of N-hydroxy-4-{2-[3-(N,N-dimethylaminomethyl)benzofuran-2-ylcarbonylamino]ethoxy}benzamide of formula (I) alone or in association with radiotherapy for use in the treatment of breast cancer, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino] ethoxy}benzamide of formula (I) or an addition salt thereof with a pharmaceutically acceptable acid or base, alone or in association with surgery for use in the treatment of epithelial ovarian carcinoma, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino] ethoxy}benzamide of formula (I) or an addition salt thereof with a pharmaceutically acceptable acid or base, alone or in association with a chemotherapy for use in the treatment of epithelial ovarian carcinoma, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to N-hydroxy-4-{2-[3-(N,N-dimethylaminomethyl)benzofuran-2-ylcarbonylamino] lethoxy}benzamide of formula (I) or an addition salt thereof with a pharmaceutically acceptable acid or base, alone or in association with a hormone therapy treatment for use in the treatment of epithelial ovarian carcinoma, characterized in that the compound of formula (I) is administered for 4 consecutive days, that period being followed by 3 consecutive days without any administration of compound of formula (I). In some embodiments, the hormone therapy treatment is tamoxifen.

The present invention relates to N-hydroxy-4-{2-[3-(N,N-dimethylaminomethyl)benzofuran-2-ylcarbonylamino] ethoxy}benzamide of formula (I) alone or in association with radiotherapy for use in the treatment of epithelial ovarian carcinoma, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of epithelial ovarian carcinoma, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of epithelial ovarian carcinoma, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of epithelial ovarian carcinoma, characterized in that the compound of formula (I) is administered for 4 consecutive days, that period being followed by 3 consecutive days without any administration of compound of formula (I). In some embodiments, the hormone therapy treatment is tamoxifen.

The present invention relates to the HCl salt of N-hydroxy-4-{2-[3-(N,N-dimethylaminomethyl)benzofuran-2-ylcarbonylamino]ethoxy}benzamide of formula (I) alone or in association with radiotherapy for use in the treatment of epithelial ovarian carcinoma, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of fallopian tube cancer, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of fallopian tube cancer, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of fallopian tube cancer, characterized in that the compound of formula (I) is administered for 4 consecutive days, that period being followed by 3 consecutive days without any administration of compound of formula (I). In some embodiments, the hormone therapy treatment is tamoxifen.

The present invention relates to N-hydroxy-4-{2-[3-(N,N-dimethylaminomethyl)benzofuran-2-ylcarbonylamino]ethoxy}benzamide of formula (I) alone or in association with radiotherapy for use in the treatment of fallopian tube cancer, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of fallopian tube cancer, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of fallopian tube cancer, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of fallopian tube cancer, characterized in that the compound of formula (I) is administered for 4 consecutive days, that period being followed by 3 consecutive days without any administration of compound of formula (I). In some embodiments, the hormone therapy treatment is tamoxifen.

The present invention relates to the HCl salt of N-hydroxy-4-{2-[3-(N,N-dimethylaminomethyl)benzofuran-2-ylcarbonylamino]ethoxy}benzamide of formula (I) alone or in association with radiotherapy for use in the treatment of fallopian tube cancer, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of primary peritoneal carcinoma, characterized in that the compound of formula (I) is administered for 4 consecutive days, that period being followed by 3 consecutive days without any administration of compound of formula (I).

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of primary peritoneal carcinoma, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of primary peritoneal carcinoma, characterized in that the compound of formula (I) is administered for 4 consecutive days, that period being followed by 3 consecutive days without any administration of compound of formula (I). In some embodiments, the hormone therapy treatment is tamoxifen.

The present invention relates to N-hydroxy-4-{2-[3-(N,N-dimethylaminomethyl)benzofuran-2-ylcarbonylamino]ethoxy}benzamide of formula (I) alone or in association with radiotherapy for use in the treatment of primary peritoneal carcinoma, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with surgery for use in the treatment of primary peritoneal carcinoma, characterized in that the compound of formula (I) is administered for 4 consecutive days, that period being followed by 3 consecutive days without any administration of compound of formula (I).

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a chemotherapy for use in the treatment of primary peritoneal carcinoma, characterized in that the compound of formula (I) is administered for 4 consecutive days, that period being followed by 3 consecutive days without any administration of compound of formula (I), with the proviso that chemotherapy is not the FOLFOX treatment regimen (folinic acid, fluorouracil, and oxaliplatin). In certain embodiments, the chemotherapy is doxorubicin. In certain embodiments, the chemotherapy is cisplatin. In certain embodiments, the chemotherapy is cyclophosphamide. In certain embodiments, the chemotherapy is cisplatin-doxorubicin-cyclophosphamide. In certain embodiments, the chemotherapy is paclitaxel. In certain embodiments, the chemotherapy is carboplatin. In certain embodiments, the chemotherapy is carboplatin and paclitaxel. In certain embodiments, the chemotherapy is pegylated liposomal doxorubicin and cisplatin.

The present invention relates to the HCl salt of N-hydroxy-4-{2-[3-(N,N-dimethylaminomethyl)benzofuran-2-ylcarbonylamino]ethoxy}benzamide of formula (I) or an addition salt thereof with a pharmaceutically acceptable acid or base, alone or in association with a hormone therapy treatment for use in the treatment of primary peritoneal carcinoma, characterized in that the compound of formula (I) is administered for 4 consecutive days, that period being followed by 3 consecutive days without any administration of compound of formula (I). In some embodiments, the hormone therapy treatment is tamoxifen.

The present invention relates to the HCl salt of N-hydroxy-4-{2-[3-(N,N-dimethylaminomethyl)benzofuran-2-ylcarbonylamino]ethoxy}benzamide of formula (I) alone or in association with radiotherapy for use in the treatment of primary peritoneal carcinoma, characterized in that the compound of formula (I) is administered for 4 consecutive days, that period being followed by 3 consecutive days without any administration of compound of formula (I).

Preferably, the N-hydroxy-4-{2-[3-(N,N-dimethylaminomethyl)benzofuran-2-yl-carbonylamino]ethoxy}benzamide is administered according to the administration regime of the invention in association with a chemotherapy or hormone therapy treatment or radiotherapy.

In certain embodiments, the N-hydroxy-4-{2-[3-(N,N-dimethylaminomethyl)benzofuran-2-ylcarbonylamino]ethoxy}benzamide is administered for 4 consecutive days, that period being followed by 3 consecutive days without any further administration of that compound, in association with a chemotherapy selected from doxorubicin, pegylated liposomal doxorubicin and cisplatin, or in association with tamoxifen as hormone therapy treatment.

In a preferred embodiment, the N-hydroxy-4-{2-[3-(N,N-dimethylaminomethyl)-benzofuran-2-ylcarbonylamino]ethoxy}benzamide is administered orally.

The useful dosage varies according to the sex, age and weight of the patient, the administration route, the nature of the cancer and any associated treatments and ranges from 30 mg/m$^2$ to 210 mg/m$^2$ of N-hydroxy-4-{2-[3-(N,N-dimethylaminomethyl)benzo-furan-2-ylcarbonylamino]ethoxy}benzamide hydrochloride per day. More generally, the useful dosage ranges from 20 mg to 480 mg of N-hydroxy-4-{2-[3-(N,N-dimethylaminomethyl)benzofuran-2-ylcarbonylamino]ethoxy}benzamide expressed as a base per day.

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference in their entirety.

A pharmaceutical composition, as used herein, refers to a mixture of a compound described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross linked croscarmellose sodium, polyvinylpyrrolidone, agar, or alginic acid or a salt thereof such as sodium alginate.

In some embodiments, solid dosage forms, e.g., pills, are prepared by mixing particles of a compound of formula (I), with one or more pharmaceutical excipients to form a bulk blend composition. When referring to these bulk blend compositions as homogeneous, it is meant that the particles of the compound of formula (I), are dispersed evenly throughout the composition so that the composition may be readily subdivided into equally effective unit dosage forms, such as pills. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986).

Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound of formula (I). In one embodiment, some or all of the particles of the compound of formula (I) are coated.

Suitable carriers for use in the solid dosage forms include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In some embodiments, disintegrants are used in a solid dosage formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm3, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, the solid dosage formulations of compound of formula (I), are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

(a) Shellac, also called purified lac, a refined product obtained from the resinous secretion of an insect. This coating dissolves in media of pH >7;

(b) Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

(c) Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 µm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions; Poly Vinyl Acetate Phthalate (PVAP). PVAP dissolves in pH >5, and it is much less permeable to water vapor and gastric fluids.

In some embodiments, the coating contains a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

BRIEF DESCRIPTION OF THE DRAWINGS

FIG. 1 shows the changes in platelet levels for administration regime 1 described in Clinical Study 1.

FIG. 2 shows the changes in platelet levels for administration regime 2 described in Clinical Study 1.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

Clinical Study 1

(N-hydroxy-4-{2-[3-(N,N-dimethylaminomethyl)benzofuran-2-yl-carbonylamino]ethoxyl}benzamide in monotherapy)

A clinical study was set up to test the toxicity and efficacy of N-hydroxy-4-{2-[3-(N,N-dimethylaminomethyl)benzofuran-2-ylcarbonylamino]ethoxy}benzamide hydrochloride. 36 patients with solid tumours were included and treated in this study. A first administration regime was tested over a cycle of three weeks, with 14 consecutive days of 2 p.o. administrations 4 hours apart, followed by a week without treatment. Four dosage levels were successively tested from 30 to 75 mg/m$^2$ (expressed as a salt) twice daily. The acceptability of the various N-hydroxy-4-{2-[3-(N,N-dimethylaminomethyl)-benzofuran-2-ylcarbonylamino]ethoxy}benzamide dose levels were evaluated (especially, haematological toxicities) at the end of the first cycle.

The results showed that all the toxicities which limited increasing the dose were grade 4 thrombopenias (blood platelet level less than 25 giga per liter), which were reversible after ceasing the N-hydroxy-4-{2-[3-(N,N-dimethylaminomethyl)benzofuran-2-ylcarbonyl-amino]ethoxy}benzamide treatment (see FIG. 1). The maximum tolerated dose according to this first administration regime was established to be 75 mg/m$^2$ twice daily.

In order to avoid the substantial reductions in the number of platelets observed using that regime, the study protocol was amended to propose a new administration regime: 4 consecutive days of 2 p.o. administrations 4 hours apart and then 3 days without treatment, that regime being applied for each of the 3 weeks corresponding to an administration cycle. This cycle can be repeated as many times as necessary for treatment of the cancer. This new regime showed less platelet toxicity than the previous regime and allowed patients to be treated at higher dose levels (90 to 105 mg/m$^2$ twice daily). By way of comparison, FIG. 2 shows that the second administration regime is substantially less detrimental than the first as regards blood platelet level at a dose of 75 mg/m$^2$ twice daily. In the second administration regime, the recommended dose and the maximum tolerated dose were established to be 90 mg/m$^2$ and 105 mg/m$^2$ twice daily, respectively.

Clinical Study 2

(N-hydroxy-4-{2-[3-(N,N-dimethylaminomethyl)benzofuran-2-yl-carbonylamino]ethoxyl}benzamide in combination with cisplatin)

A phase I clinical study for testing the association of N-hydroxy-4-{2-[3-(N,N-dimethylaminomethyl)benzofuran-2-ylcarbonylamino]ethoxy}benzamide hydrochloride with cisplatin is carried out on about forty patients with various solid tumours. The patients receive a maximum of six cycles of treatment with the association, each of the cycles taking the following form: the N-hydroxy-4-{2-[3-(N,N-dimethylaminomethyl)benzofuran-2-ylcarbonylamino]ethoxy}benzamide hydrochloride is administered for 4 consecutive days followed by 3 consecutive days without treatment, that being carried out for the first two weeks of a cycle of three weeks. The cisplatin is administered on the third day of each treatment cycle. No treatment is administered during the third week of the cycle. On the relevant days, the daily dose of N-hydroxy-4-{2-[3-(N,N-dimethyl-aminomethyl)benzofuran-2-ylcarbonylamino]ethoxy}benzamide hydrochloride is between 80 and 320 mg inclusive (expressed as a base), comprising two p.o. administrations 4 hours apart. The cisplatin is administered at a fixed dose of 75 mg/m$^2$.

At the end of a treatment cycle, the toxicity of the protocol involving N-hydroxy-4-{2-[3-(N,N-dimethylaminomethyl)benzofuran-2-ylcarbonylamino]ethoxy}benzamide hydrochloride and cisplatin in association is evaluated. If no prohibitive toxicity is observed, the patient continues the treatment. Every two cycles, the efficacy of the treatment is assessed via evaluation of the tumour response (CT scan, MRI, . . . ). The acceptability profile is also evaluated (especially, haematological and cardiac toxicities). The patient continues the combination treatment for a maximum of six cycles.

Clinical Study 3

(N-hydroxy-4-{2-[3-(N,N-dimethylaminomethyl)benzofuran-2-yl-carbonylamino]ethoxy}benzamide in combination with doxorubicin)

A phase I clinical study for testing the association of N-hydroxy-4-{2-[3-(N,N-dimethylaminomethyl)benzofuran-2-ylcarbonylamino]ethoxy}benzamide hydrochloride with doxorubicin in the treatment of advanced solid tumours is carried out on about forty patients. The patients receive a maximum of six cycles of treatment with the association, each of the cycles taking the following form: the N-hydroxy-4-{2-[3-(N,N-dimethylaminomethyl)benzofuran-2-ylcarbonylamino]ethoxy}benzamide hydrochloride is administered for 4 consecutive days followed by 3 consecutive days without treatment, that being carried out for the first three weeks of a cycle of four weeks. The doxorubicin is infused on the third day of the first three weeks of the cycle. No treatment is administered during the fourth week of the cycle.

On the relevant days, the daily dose of N-hydroxy-4-{2-[3-(N,N-dimethyl-aminomethyl)benzofuran-2-ylcarbonylamino]ethoxy}benzamide hydrochloride is between 60 and 150 mg/m$^2$ inclusive (expressed as a salt), comprising two p.o. administrations 4 hours apart. The doxorubicin is administered at a fixed dose of 25 mg/m$^2$.

At the end of a treatment cycle, the toxicity of the protocol involving N-hydroxy-4-{2-[3-(N,N-dimethylaminomethyl)benzofuran-2-ylcarbonylamino]ethoxy}benzamide hydrochloride and doxorubicin in association is evaluated. If no prohibitive toxicity is observed, the patient continues the treatment. Every two cycles, the efficacy of the treatment is assessed via evaluation of the tumour response (CT scan, MRI, . . . ). The acceptability profile is also evaluated (especially, haematological and cardiac toxicities). The patient continues the combination treatment for a maximum of six cycles.

Clinical Study 4

(N-hydroxy-4-{2-[3-(N,N-dimethylaminomethyl)benzofuran-2-yl-carbonylamino]ethoxy}benzamide in combination with pegylated liposomal doxorubicin)

A phase I clinical study for testing the association of N-hydroxy-4-{2-[3-(N,N-dimethylaminomethyl)benzofuran-2-ylcarbonylamino]ethoxy}benzamide hydrochloride with pegylated liposomal doxorubicin in the treatment of primary platinum-resistant and partially platinum-sensitive, epithelial ovarian, fallopian tube or primary peritoneal carcinoma is carried out on about seventy patients. The patients are subjected to cycles of treatment of four weeks with the association. Two schedules are tested:

Schedule 1: the N-hydroxy-4-{2-[3-(N,N-dimethylaminomethyl)benzofuran-2-ylcarbonylamino]ethoxy}benzamide hydrochloride is administered for 4 consecutive days followed by 3 consecutive days without treatment, that being carried out for the first three weeks of a cycle of four weeks. The pegylated liposomal doxorubicin is infused on the third day of the first week of the cycle. No treatment is administered during the fourth week of the cycle.

Schedule 2: the N-hydroxy-4-{2-[3-(N,N-dimethylaminomethyl)benzofuran-2-ylcarbonylamino]ethoxy}benzamide hydrochloride is administered for 4 consecutive days followed by 3 consecutive days without treatment in the first week of a cycle of four weeks. The pegylated liposomal doxorubicin is infused on the third day of the first week of the cycle. No treatment is administered during the three last weeks of the cycle.

On the relevant days, the daily dose of N-hydroxy-4-{2-[3-(N,N-dimethyl-aminomethyl)benzofuran-2-ylcarbonylamino]ethoxy}benzamide hydrochloride is between 60 and 150 mg/m² inclusive (expressed as a salt), comprising two p.o. administrations 4 hours apart. The pegylated liposomal doxorubicin is administered at a fixed dose of 40 mg/m².

At the end of a treatment cycle, the toxicity of the protocol involving N-hydroxy-4-{2-[3-(N,N-dimethylaminomethyl)benzofuran-2-ylcarbonylamino]ethoxy}benzamide hydrochloride and pegylated liposomal doxorubicin in association is evaluated. If no prohibitive toxicity is observed, the patient continues the treatment. Every two cycles, the efficacy of the treatment is assessed via evaluation of the tumour response (CT scan, MRI, . . . ). The acceptability profile is also evaluated (especially, haematological and cardiac toxicities).

Clinical Study 5

(N-hydroxy-4-{2-[3-(N,N-dimethylaminomethyl)benzofuran-2-yl-carbonylamino]ethoxy}benzamide in combination with tamoxifen)

A phase I clinical study for testing the association of N-hydroxy-4-{2-[3-(N,N-dimethylaminomethyl)benzofuran-2-ylcarbonylamino]ethoxy}benzamide hydrochloride with tamoxifen in the treatment of advanced breast cancer is carried out on about forty patients. The patients are subjected to cycles of treatment with the association, each of the cycles taking the following form: the N-hydroxy-4-{2-[3-(N,N-dimethylaminomethyl)benzofuran-2-ylcarbonylamino]ethoxy}benzamide hydrochloride is administered for 4 consecutive days followed by 3 consecutive days without treatment. The tamoxifen is administered daily throughout the duration of the treatment.

On the relevant days, the daily dose of N-hydroxy-4-{2-[3-(N,N-dimethyl-aminomethyl)benzofuran-2-ylcarbonylamino]ethoxy}benzamide hydrochloride is between 160 and 320 mg inclusive (expressed as a base), comprising two p.o. administrations 4 hours apart. The tamoxifen is administered at a fixed dose of 20 mg. At the end of two treatment cycles, the toxicity of the protocol involving N-hydroxy-4-{2-[3-(N,N-dimethylaminomethyl)benzofuran-2-ylcarbonylamino]ethoxy}benzamide hydrochloride and tamoxifen in association is evaluated. If no prohibitive toxicity is observed, the patient continues the treatment. Every two cycles, the efficacy of the treatment is assessed via evaluation of the tumour response (CT scan, MRI, . . . ). The acceptability profile is also evaluated (especially, haematological and cardiac toxicities).

The various clinical studies hereinbefore show that an administration regime in which N-hydroxy-4-{2-[3-(N,N-dimethylaminomethyl)benzofuran-2-ylcarbonylamino]ethoxy}-benzamide is administered for 4 consecutive days, that period being followed by 3 consecutive days without any administration, makes it possible to minimise the platelet toxicity inherent to the product and thereby to increase the therapeutic dose for the treatment of cancer.

The invention claimed is:

1. A method of treating cancer in a subject in need thereof; comprising administration of an effective amount of N-hydroxy-4-{2-[3-(N,N-dimethylaminomethyl)benzofuran-2-ylcarbonylamino]ethoxy}benzamine of formula (I):

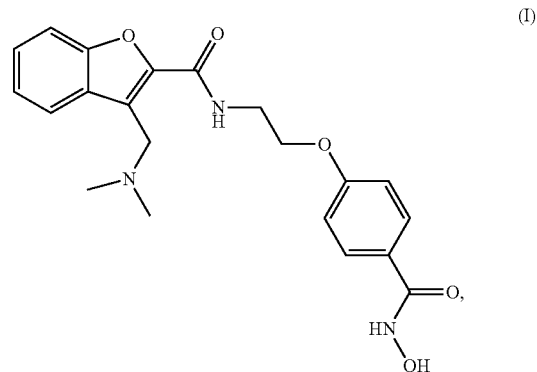 [SMILES: CN(C)Cc1c(C(=O)NCCOc2ccc(C(=O)NO)cc2)oc2ccccc12]

or an addition salt thereof with a pharmaceutically acceptable acid or base; alone or in combination with a surgery, chemotherapy, hormone therapy treatment or radiotherapy. wherein the compound of formula (I), or an addition salt thereof with a pharmaceutically acceptable acid or base. is administered for 4 consecutive days, that period being followed by 3 consecutive days without any administration of the compound of formula (I), or an addition salt thereof with a pharmaceutically acceptable acid or base, with the proviso that the chemotherapy is not FOLFOX (oxaliplatin/folinic acid/5-fluorouracil).

2. The method according to claim 1, wherein the compound of formula (I) is administered in the form of a hydrochloride.

3. The method according to claim 1, wherein the compound of formula (I), or an addition salt thereof with a pharmaceutically acceptable acid or base, is administered for 4 consecutive days at a rate of 2 administrations per day, that period being followed by 3 consecutive days without any administration of the compound of formula (I).

4. The method according to claim 1, wherein the compound of formula (I), or an addition salt thereof with a pharmaceutically acceptable acid or base, is administered in combination with a chemotherapy, hormone therapy treatment, or radiotherapy.

5. The method according to claim 1, wherein the cancer is carcinoma, tumours, neoplasm lymphoma, melanoma, glioma, sarcoma, or blastoma.

6. The method according to claim 1, wherein the cancer comprises solid tumours.

7. The method according to claim 1, wherein the cancer is breast cancer.

8. The method according to claim 1, wherein the cancer is ovarian carcinoma, fallopian tube carcinoma, or prima peritoneal carcinoma.-

9. The method according claim 1, wherein the chemotherapy treatment is cisplatin, doxorubicin or pegylated liposomal doxorubicin.

10. The method according to claim 1, wherein the hormone therapy treatment is tamoxifen.

* * * * *